(12) United States Patent
Pargass et al.

(10) Patent No.: US 6,572,596 B2
(45) Date of Patent: Jun. 3, 2003

(54) CONVERTIBLE DIAPER

(75) Inventors: Sunita Pargass, Norcross, GA (US); Ellyn L. Conger, Macon, GA (US); Stacy Yeater, Alpharetta, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/854,501

(22) Filed: May 15, 2001

(65) Prior Publication Data

US 2002/0173765 A1 Nov. 21, 2002

(51) Int. Cl.⁷ .................................. A61F 13/15
(52) U.S. Cl. .................... 604/385.01; 604/385.24; 604/385.28
(58) Field of Search .................. 604/317–402, 604/385.01, 385.24, 385.25, 385.26, 385.27, 385.28, 385.29; 2/400–406, 236, 237

(56) References Cited

U.S. PATENT DOCUMENTS

| | | |
|---|---|---|
| 4,771,483 A | 9/1988 | Hooreman et al. |
| 5,144,697 A * | 9/1992 | Sandbeck .................. 2/236 |
| 5,275,590 A | 1/1994 | Huffman et al. |
| 5,281,207 A | 1/1994 | Chmielewski et al. |
| 5,292,316 A | 3/1994 | Suzuki |
| 5,439,458 A | 8/1995 | Noel et al. |
| 5,607,416 A * | 3/1997 | Yamamoto et al. ......... 604/397 |
| 5,660,664 A | 8/1997 | Herrmann |
| 5,843,068 A | 12/1998 | Allen et al. |
| 5,870,778 A | 2/1999 | Tharpe |
| 5,931,825 A * | 8/1999 | Kuen et al. ............... 604/385.2 |
| 6,123,694 A | 9/2000 | Pieniak et al. |
| 6,176,952 B1 | 1/2001 | Maugans et al. |

FOREIGN PATENT DOCUMENTS

GB  2130076  * 5/1984

* cited by examiner

Primary Examiner—Jeanette Chapman
(74) Attorney, Agent, or Firm—Hunton & Williams

(57) ABSTRACT

The invention comprises an absorbent garment and a method for making an absorbent garment. An absorbent garment is provided comprising elastic side belts attached at an angle to the main body of the garment to provide a better fit to the user. Adjustment strips preferably are affixed to the elastic side belts and to the main body of the garment to allow the user to repeatedly adjust the garment while the garment is being worn. A method for making the absorbent garment also is disclosed.

17 Claims, 3 Drawing Sheets

Fig. I

CONVERTIBLE DIAPER

BACKGROUND OF THE INVENTION

1. Field of the Invention

The present invention relates to absorbent garments. Specifically, this invention relates to an absorbent garment having elastic side belts with adjusting strips that may be adjusted while the garment is in use.

2. Description of Related Art

Present-day all-in-one diapers are being replaced to an ever greater extent with pants-type diapers, or so-called training pants, for slightly older diaper-wearing children. Pants-type diapers have a number of good features. For example, pants-type diapers resemble conventional underpants and, thereby, can help somewhat older diaper-wearing children to learn to perform the operations required to put on conventional underpants as well as encourage the child to graduate to underpants. However, present garments can be difficult to put on, especially by young children. Furthermore, such garments are subject to loosening during use and may not fit smaller users very well.

Several efforts have been made to develop an absorbent garment/pants-type diaper with stretchable side panels. U.S. Pat. No. 5,843,068, the disclosure of which is incorporated by reference herein in its entirety, discloses a pants-type diaper comprising elastic side panels interconnecting front and back sections of a backsheet. The elastic side panels are a composite of dissimilar layers that are bonded together. The elastic side panels extend over a substantial distance along the lateral edges of the backsheet and have long bond seams joining the panels. Such a construction provides substantially more side coverage of a user than a belt, leading to less direct breathability. Furthermore, the panels' greater size and longer bond seams create smaller leg holes, which causes greater difficulty for a user attempting to put a foot through the leg hole; particularly for a younger user attempting to use the absorbent garment as a training pant without assistance. Additionally, the pants- or brief-type diaper disclosed in U.S. Pat. No. 5,843,068 does not have a mechanism to adjust the fit of the diaper once the user is wearing the diaper.

U.S. Pat. No. 4,771,483, the disclosure of which is incorporated by reference herein in its entirety, discloses a diaper comprising a rectangular sheet. Partial, parallel lengthwise cuts are made in the sheet to form rectilinear slits. Pieces of elongated elastic are affixed to the lengthwise edges. When relaxed, the elastic gathers the rectangular sheet causing the slits to form leg holes and the elastic to form side belts. U.S. Pat. No. 4,771,483 does not, however, disclose a mechanism for adjusting the fit of the diaper while the user is wearing the diaper. Further, the pieces of elongated elastic are affixed directly to the sheet, which is believed to have the disadvantage of causing a poor fit for the diaper by permitting the formation of gaps between the diaper and the user at the ends of the rectilinear slits.

Accordingly, there exists a need to develop an absorbent garment having elastic side belts that may be used as a pants-type diaper. A need exists for such a garment to have leg holes of sufficient size to allow easier operation by a user; particularly a younger user inexperienced with the use of brief- or pants-type diapers. Further, a need exists for a garment providing the better fit allowed by elastic side panels while simultaneously providing breathability at the sides of the garment. There also exists a need for an absorbent garment with a specific bond and cut angle at the end of an elastic side belt to provide the user with a better fitting garment. Additionally, a need exists for a mechanism to adjust the fit of the garment; particularly once the user is wearing same. There also is a need to manufacture such a garment at a low cost.

SUMMARY OF THE INVENTION

An embodiment of the present invention provides an absorbent garment having a main body with front and rear waist edges, left and right side edges, and angular edges joining each of the side edges to the front and rear edges. The angular edges on the left side of the garment are joined to a left elastic side belt, and the angular edges on the right side of the garment are joined to a right elastic side belt. The garment may also comprise additional features, such as elastic leg gathers and standing leg gathers.

The angle of the bond used to attach the side belts to the main body has the advantage of preventing the garment from pulling away or uncomfortably gathering around the waist of the user. In one embodiment of the invention, adjustment strips are affixed to the elastic side belts that may be attached to a portion of the main body to loosen or tighten the garment to better fit the user. Such adjustments may be made by the user while the garment is being worn.

There also is provided a method of forming a garment comprising providing a continuous supply of main body material along the machine direction, cutting leg holes from the sides of the main body material, and providing a supply of elastic side belt material along each of the side edges of the main body material such that the elastic side belt material overlays the main body material. The elastic side belt material is bonded to the main body material in bond regions that are oriented at an angle to the machine direction, and excess portions of the elastic side belt material and main body material may be cut away from the assembly. Substantially complete diapers are severed from the assembly. Using this method, the garment may be manufactured entirely in the machine direction, providing faster, less expensive, and more efficient manufacturing.

These and other objects, features and advantages of various embodiments of this invention will become evident from the following description of the preferred embodiments of this invention, with reference to the accompanying drawings.

BRIEF DESCRIPTION OF THE DRAWINGS

The present invention may be understood more readily by viewing the drawings, in which.

DETAILED DESCRIPTION

As used herein, the terms "absorbent garment" and "garment" refer to items that absorb and contain fluid discharges and exudates, and more specifically refer to garments that are placed against or in proximity to the body of the user to absorb and contain various bodily discharges. A non-exhaustive list of examples of absorbent garments includes diapers, diaper cores, diaper covers, disposable diapers, training pants, feminine hygiene products and adult incontinence products. The claims are intended to cover all of the forgoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above.

Figure 1:
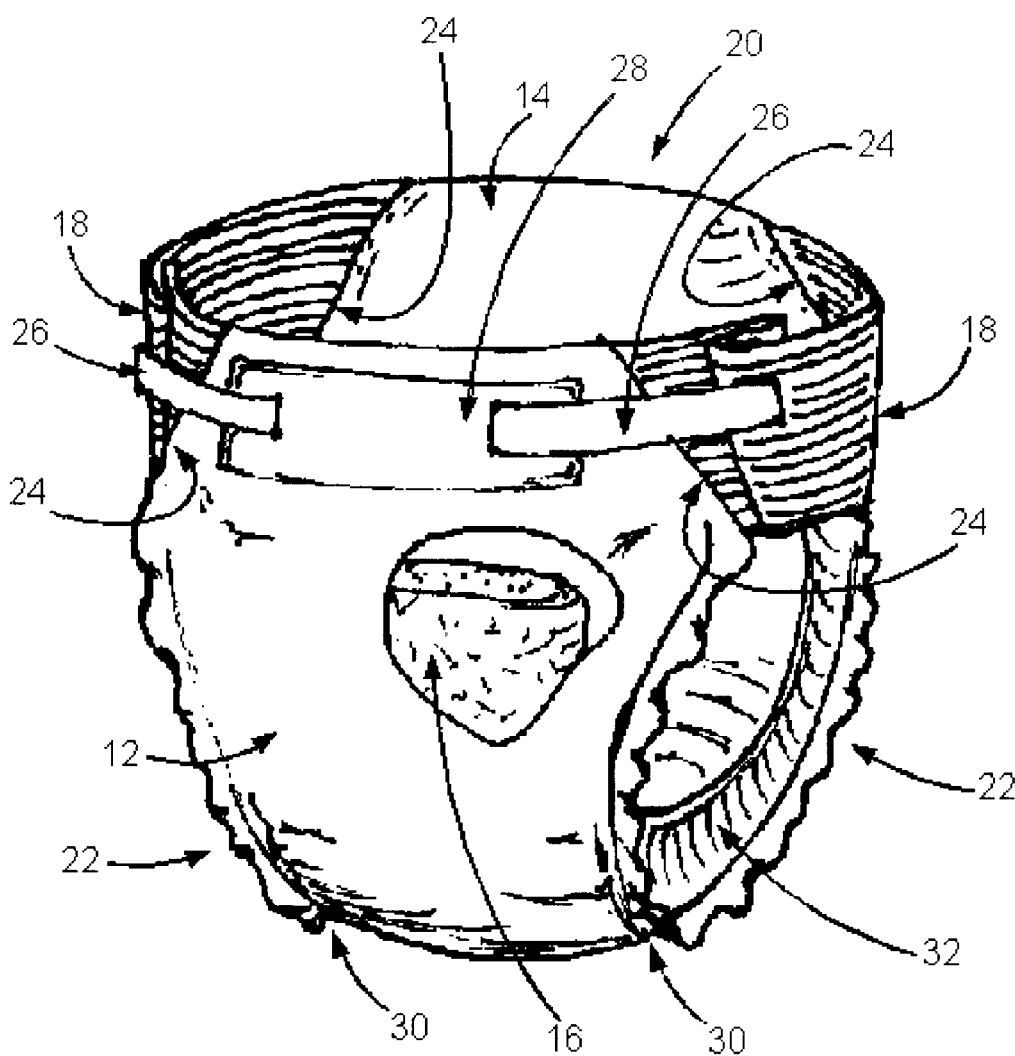
FIG. 1 depicts an embodiment of the present invention as it appears when worn by a user, with the backsheet partially cut away to show the absorbent core.

FIG. 1 depicts an embodiment of the present invention as it appears when worn by a user, with the main body partially cut away to show the absorbent core. In the depicted embodiment, the garment 10 is comprised of a main body having an exterior facing moisture impervious outer layer 12 or "backsheet," and a moisture pervious body-contacting inner layer 14 or "topsheet." An absorbent core 16 is disposed between the topsheet 14 and the backsheet 12. In the embodiment depicted in FIG. 1 the backsheet 12, topsheet 14, and core 16 comprise the main body of the garment, however in another embodiment of the invention the main body may be made from a separate sheet and the backsheet 12, topsheet 14, and core 16 may be assembled separately then attached to the main body.

The garment preferably further comprises an elastic side belt 18 ("belt") located on each side of the garment 10. Each belt 18 is connected to and extends between the front an rear portions of one side of the garment 10 to form a waist hole 20, and leg holes 22. The belts 18 are joined to the main body of the garment along seams 24, which are angled to provide an improved fit on the wearer.

Each elastic side belt 18 may also have an adjustment strip 26 attached to it for adjusting the fit of the garment while it is being worn by a user. The adjustment strip may operate by interacting with an adjuster attachment area 28 to provide a secure connection.

In the embodiment of the present invention depicted in FIG. 1, the garment 10 further comprises various mechanisms for improving the fit of the garment 10 such as leg gathers 30 and standing leg gathers 32. Such gathers can be used to contract the leg holes 22 around the wearer's legs and body to prevent leakage. A garment 10 of the present invention may also comprise elastic or other fitting devices in the waist portions or other portions of the main body to help contain body exudates.

The various parts of the garment 10 are operatively associated with one another in such a manner that the garment will maintain its desired structure during use. The parts may be operatively associated with one another by a variety of methods known in the art, including, but not limited to: using adhesives such as hot melt adhesives and construction adhesives, chemical or solvent bonding, ultrasonic welding, stitching, heat bonding, or any other method of affixation known or hereafter discovered. All of the parts may be joined to each adjacent part, but some parts may not be joined to others. In one embodiment, the topsheet 14 and backsheet 12 are bonded to one another around their perimeter regions, thereby encasing and holding the absorbent core 16 in place without having to directly join the absorbent core 16 to any parts of the garment 10. The topsheet 14 or backsheet 12 may also be operatively associated with the absorbent core 16. As understood herein, the term "operatively associated" includes directly joining one part to another, indirectly joining parts together through one or more intermediary parts, whether those intermediary parts are described herein or not, joining parts in such a manner that unjoined parts are captured or held in their proper place, and any other suitable joining means that maintains the structural integrity of the garment 10 for the duration of its use.

Figure 2:
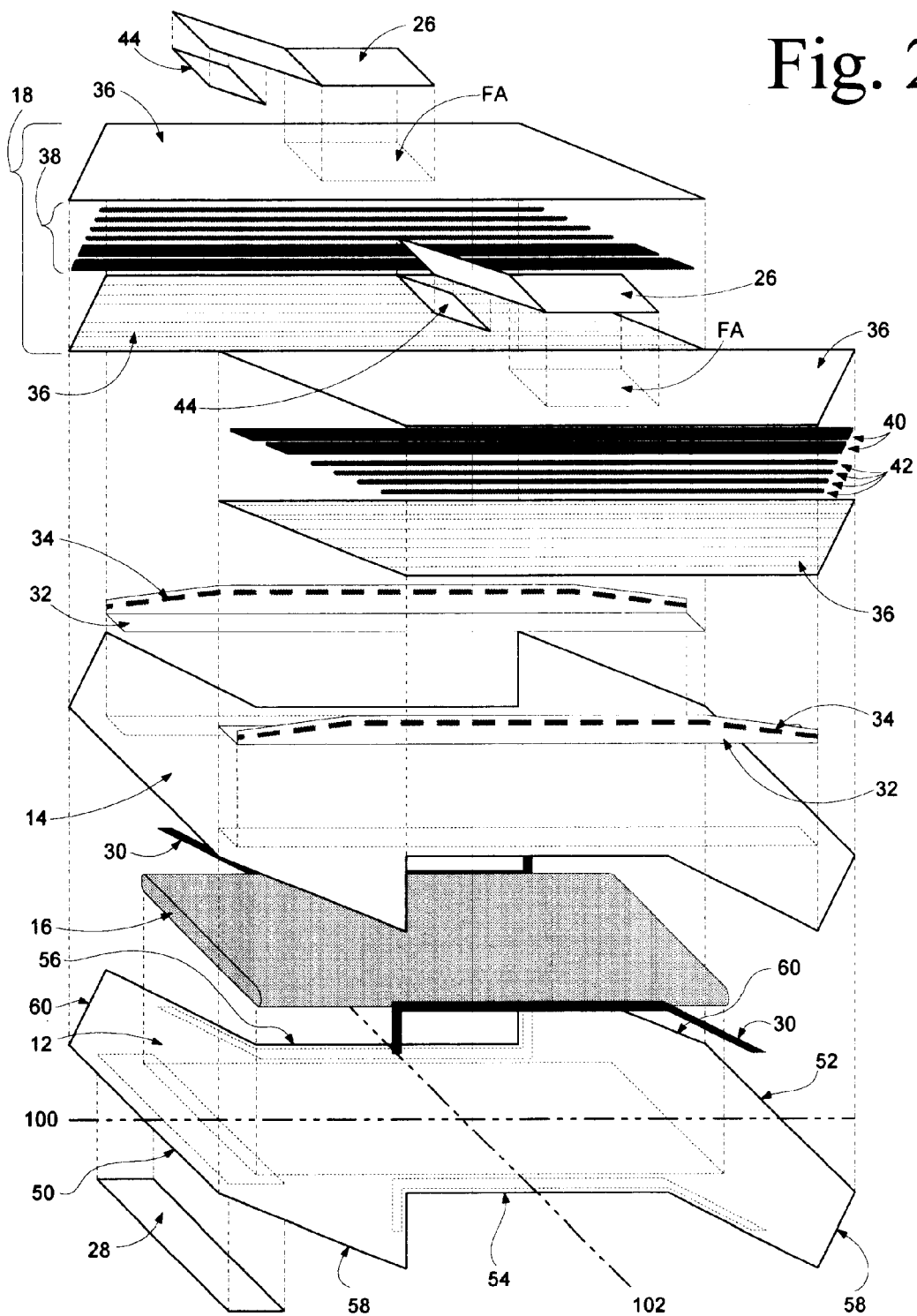
FIG. 2 is an exploded view of an embodiment of the present invention with elastic members shown in the elongated position for clarity, and the garment laid flat.

FIG. 2 is an exploded view of an embodiment of the present invention with elastic members shown in the elongated position for clarity, and the garment laid flat. The garment 10 has a longitudinal axis 100 corresponding approximately to the rear-to-front axis of the wearer, and a lateral axis 102, orthogonal to the longitudinal axis 100, and corresponding approximately to the side-to-side axis of the wearer. In one embodiment of the invention the longitudinal axis 100 of the garment 10 is approximately parallel with the machine direction of the garment 10.

In the embodiment of the invention depicted in FIG. 2, the main body of the garment comprises a backsheet 12 and topsheet 14 having substantially identical dimensions. The perimeter of the main body of the garment is defined by a laterally extending front waist edge 50, a laterally extending rear waist edge 52, a longitudinally extending left side edge 54, a longitudinally extending right side edge 56, left angular edges 58 joining the longitudinally extending left side edge 54 to the laterally extending front waist edge 50 and the laterally extending rear waist edge 52, and right angular edges 60 joining the longitudinally extending right side edge 56 to the laterally extending front waist edge 50 and the laterally extending rear waist edge 52. The side belts 18 are joined to the main body of the garment at the left and right angular edges 58, 60 to form the side seams 24 (FIG. 1) of the garment 10.

The backsheet 12 is preferably made from a substantially liquid impervious material. The selection and manufacture of such materials is well known in the art, and is disclosed, for example, in U.S. Pat. No. 6,123,694 issued to Peniak et al., and U.S. Pat. No. 6,176,952 issued to Maugans et al., each of which is incorporated herein by reference in its entirety, and in a manner consistent with the present invention. In one embodiment, the backsheet 12 is made from a thin thermoplastic material, such as a pigmented polyethylene film having a thickness in the range of 0.02–0.04 mm. The backsheet 12 may also have a laminate construction comprising one or more layers of meltblown polypropylene or meltblown polyethylene, sandwiched between layers of spun-bonded material (often referred to as an "SMS" laminate). Additional layers may be added to the backsheet 12 in order to provide the backsheet 12 with other desirable properties, such as to improve the tactile feel, or "hand," of the backsheet 12. The backsheet 12 may also be entirely or partly gas pervious to allow the garment to circulate air, or "breathe." In one embodiment of the invention, the backsheet 12 has a "multi-panel" construction in which the backsheet 12 comprises several pieces of material, which may have dissimilar physical properties, joined at or near their edges with little or no overlap.

The backsheet 12 may define the outer perimeter of the main body of the garment, such that none of the other parts of the garment 10, except for the side belts 18, extend beyond the outline of the backsheet 12 when the main body of the garment is laid flat, as is depicted in the embodiment of FIG. 2. However, in other embodiments the backsheet 12 may not define the outer perimeter of the garment, and other parts may extend beyond the edges of the backsheet 12.

The topsheet 14, which preferably overlays and is operatively associated with the backsheet 12, can be made from a substantially liquid pervious material to allow body exudates to penetrate into the absorbent core 16, which is disposed between the topsheet 14 and the backsheet 12. The topsheet 14 may typically be comprised of a carded polyester fiber with a latex binder or of a spun-bonded polypropylene having continuous fibers and thermally bonded by patterned calendar rolls. The topsheet 14 may be treated over all or part of its surface to render it hydrophilic. The topsheet 14 may also be zone-treated with a surfactant to render it hydrophilic only in certain target areas. The topsheet 14 may also be treated with skin treating ingredients, such as aloe, vitamin E, and the like. The surface treatment can be accomplished by a variety of methods known in the art. The topsheet 14 may also comprise an apertured material, such as an apertured film.

In one embodiment of the present invention, the topsheet 14 comprises a laminate of several layers of material, which may have different physical properties. In another embodiment, the topsheet 14 is made from several pieces of material joined at or near their edges with little or no overlap, which may have dissimilar physical properties (multi-panel construction). Such an embodiment is disclosed, for example, in U.S. Pat. No. 5,275,590 issued to Huffman et al., which is incorporated herein by reference in its entirety, and in a manner consistent with the present invention.

In the embodiment of the invention depicted in FIG. 2, the topsheet 14 has substantially the same planar dimensions as the backsheet 12, such that the perimeter of the topsheet 14 matches the perimeter of the backsheet 12. In other embodiments, the topsheet 14 may be larger or smaller than the backsheet 12, and may have a different general shape. In one embodiment, the topsheet 14 is large enough to completely cover all of the parts of the garment that are sandwiched between the topsheet 14 and the backsheet 12, such as the leg gathers 30, and absorbent core 16.

In one embodiment of the present invention, the topsheet 14 is operatively associated with the backsheet 12 around the perimeter of the topsheet 14. In this embodiment, the topsheet 14 and backsheet 12 may be operatively associated with one another by using hot melt adhesives, ultrasonic bonding, or any other suitable method known in the art. Also in this embodiment, the topsheet 14 and backsheet 12 may be bonded to one another in substantially all areas not having intermediately placed parts, such that some or all of the intermediately placed, or "sandwiched," parts are physically captured between the topsheet 14 and backsheet 12, but not bonded to the backsheet 12 or topsheet 14.

An absorbent core 16 is preferably sandwiched between the inner surfaces of the backsheet 12 and the topsheet 14. The absorbent core 16 may be comprised of one or more layers of material, such as an absorbent layer for storing fluids and an acquisition layer for distributing fluids. Such multiple layer absorbent cores are known in the art and disclosed in U.S. Pat. No. 5,439,458 issued to Noel et al., which is incorporated herein by reference in its entirety, and in a manner consistent with the present invention.

The absorbent core 16 may be made from any absorbent material or materials known in the art. In one embodiment of the invention, the absorbent core 16 comprises wood fibers or other fibers such as chemical wood pulp, or any other suitable liquid absorbing material, such as commercially available fluff pulp or fluffed bleached kraft softwood pulp. In another embodiment of the invention, the absorbent core 16 comprises a combination of a porous fibrous web and super absorbent particles. Such absorbent cores are known in the art and are disclosed, for example, in U.S. Pat. No. 5,281,207 issued to Chmielewski et al., which is incorporated herein by reference in its entirety, and in a manner consistent with the present invention. In such an embodiment, the absorbent core 16 may be surrounded by a liquid pervious tissue over-wrap, or other material.

The absorbent core 16 is generally elongated along the longitudinal axis 100 of the garment, and may extend along either or both of the lateral and longitudinal axes 102, 100 to the outer perimeter of the garment. In the embodiment depicted in FIG. 2, the absorbent core 16 is substantially rectangular in shape, however, it may also have rounded ends or other shapes, such as an "I" shape or a "T" shape. The absorbent core 16 may also have channels, grooves or pockets, and may have a varying thickness.

The garment 10 of the present invention may include various mechanisms for improving the fit of the garment 10 to the wearer, and for improving leakage resistance. In one embodiment of the invention, leg gathers 30 are used to contract the leg holes 22 of the garment 10 around the wearer's legs to prevent body waste from escaping. In one embodiment, leg gathers 30 are incorporated into the garment 10 by extending one or more pieces of elastic and bonding them to the topsheet 14, backsheet 12, or other components while the elastic is in an elongated state. When the elastic contracts, the parts of the garment to which the leg gathers 30 are attached constrict around the user's body. The elastic elements may be made from natural rubber, lycra, polyurethane, heat shrinkable polymer ribbons, or any other suitable elastic material or composite. Leg gathers are known in the art, and U.S. Pat. No. 5,660,664 issued to Hermann, which is incorporated herein by reference in its entirety, and in a manner consistent with the present invention, discloses an exemplary method of manufacturing leg gathers.

In another embodiment of the invention the garment 10 is equipped with standing leg gathers 32. Standing leg gathers 32 generally are comprised of flaps or sleeves of liquid impervious material that have one or more elastic elements 34 in them. The flaps are drawn against the user's body by the contracting force of the elastic, and help seal the garment 10 against leakage. The elastic elements 34 may comprise any suitable elastic material, and the flap portions of the leg gathers 32 may be made as an integral part of the topsheet 14 or backsheet 12, or from additional fabric material that may or may not be liquid pervious. Standing gathers are disclosed, for example, in U.S. Pat. No. 5,292,316 issued to Suzuki, which is incorporated herein by reference in its entirety, and in a manner consistent with the present invention.

Still referring to FIG. 2, the garment of the present invention further comprises a pair of elastic side belts 18. Each belt 18 may be attached to the main body of the garment at two seams 24 (FIG. 1), which are oriented at an angle to the longitudinal axis 100 of the garment. Each belt 18 preferably comprises one or more elastic elements 38 that contract the belt 18 to hold the garment 10 on the user. The belts 18 may be attached to the main body of the garment such that the elastic elements 38 are in an extended position when the garment is in a flattened position. This may be accomplished by extending the elastic elements 38 before they are attached to the main body of the garment during the assembly of the garment, by activating heat-activated elastic elements after being constructed in a relaxed position, or by any other method known in the art.

The elastic elements 38 may be disposed between layers of sheet material 36 in an extended position, such that when the elastic elements 38 contract they gather the layers of sheet material 36. An example of disposing elastic elements between layers of sheet material is disclosed in U.S. Pat. No. 5,870,778 issued to Tharpe, which is incorporated herein by reference in its entirety, and in a manner consistent with the present invention. Other structures may also be used for the belts 18. In one embodiment of the invention, the layers of sheet material 36 are comprised of a nonwoven material, such as the materials described above with regard to the topsheet 14 and backsheet 12. The layers of sheet material 36 may also be made, however, from any other suitable material. In one embodiment, the material for the layers of sheet material 36 are selected to provide a good tactile impression, or "hand," to provide a comfortable fit. In another embodiment of the invention, the materials for the layers of sheet material 36 are selected to be gas permeable to improve the breathability of the garment 10. In yet another embodiment of the invention, the inner and outer layers of sheet material 36 are comprised of materials having different physical properties. In one embodiment, the elastic elements 38 are stretched to between about 100% to about 350% of their relaxed length and encased between two sheets of nonwoven material.

The elastic elements 38 may comprise any suitable synthetic or natural elastic material, such as natural rubber, lycra, polyurethane, and heat-activated polymeric elastics. The elastic elements 38 may also be provided in any suitable elastic structure, such as ribbons, membranes, strands, meshes, foams, and aggregates.

The elastic elements 38 may be selected to provide a greater or lesser contracting force for different parts of the belts 18. For example, elastics having a high contracting force may be selected for the regions of the elastic belts 18 nearest the users waist, and elastics having a lesser contracting force may be selected for those parts of the belts 18 around the user's hips. Such differences in contracting force may be obtained by providing elastic elements 38 having differing cross sectional shapes, by providing elastic elements 38 made from different materials, by providing a greater or lesser number of elastic elements 38, or by any other method known in the art. In the embodiment of the invention depicted in FIG. 2, there are several waist elastics 40, providing a greater contracting force in the belts 18 near the user's waist, and several hip elastics 42, providing a lesser contracting force in the belts 18 near the user's hips.

The belts 18 preferably are operatively associated with the main body of the garment at seams 24 (FIG. 1) that are at angles relative to the longitudinal axis 100 of the garment 10. In one embodiment, the seams 24 (FIG. 1) are the only places at which the belts 18 are operatively associated with the main body of the garment. In one embodiment, the main body of the garment comprises a topsheet 14, an absorbent core 16 and a backsheet 12, and the belts 18 are attached to the backsheet 12 of the garment 10. In another embodiment, the main body of the garment comprises a separate sheet of material to which the topsheet 14, absorbent core 16 and backsheet 12 are affixed, and the belts 18 are attached to the separate sheet that forms the main body. As described in more detail elsewhere herein, the belts 18 may be operatively associated with the main body of the garment in any manner known in the art.

The angles at which the belts 18 are joined to the main body of the garment are selected to optimize user comfort and leakage prevention. The angles may also be different for the front seams 24 (FIG. 1) and the rear 30 seams 24 (FIG. 1). If the angle relative to the longitudinal axis is relatively great, then larger leg holes 22 will be provided. Greater angles also tend to cause the portion of the belts 18 closest to the leg hole 22 to be looser; a problem that may be at least partly overcome by providing elastic elements 38 with a higher contracting force in those regions, or with a lesser contracting force in the other regions of the belts 18. If the angle is relatively small, then smaller leg holes will be provided, and the belts 18 will be looser around the user's waist. Again, problems with looseness can be at least partially solved by adjusting the contracting forces of the elastic elements 38. The size of the belts 18 in the lateral axis 102 of the garment 10 also contributes to looseness or tightness variations in the belts 18, with wider belts 18 tending to exacerbate the differences in tightness. In one embodiment of the invention, the seams 24 (FIG. 1) are oriented at an angle of between about 10 degrees and about 80 degrees relative to the longitudinal axis 100 of the garment. In another embodiment, the seams 24 (FIG. 1) are oriented at an angle of between about 30 degrees and about 60 degrees relative to the longitudinal axis 100 of the garment. In yet another embodiment, the seams 24 (FIG. 1) are oriented at an angle of about 45 degrees relative to the longitudinal axis 100 of the garment.

In order to provide good manufacturability, fit, comfort, and leakage prevention, the width of the belts 18, contracting forces of the elastic elements 38, and angles of the bonds 24 may all be adjusted.

It is anticipated that good results may be obtained from an embodiment of the invention in which the belts 18 are attached to the main body of the garment at angles of between about 30 and about 60 degrees at both the front and rear seams 24 (FIG. 1); have substantially no variation in the contracting force of the elastic elements 38 across the width (i.e., lateral axis 102 dimension) of the belts 18; and have a width of between about 40 mm and about 100 mm; and more preferably between about 55 mm and about 85 mm, and most preferably of about 70 mm. Providing several waist elastics 40 having a slightly higher contracting force than the hip elastics 42 may also improve the fit of the garment in this embodiment.

Referring back to FIG. 2, adjustment strips 26 may be disposed on and partially attached to the belts 18 to provide for an adjustable fit. Absorbent garments often loosen during use for various reasons, such as inelastic stretching of the various components, changes in user size, and increased loading caused by the release of body exudates into the garment 10. A portion of the adjustment strips 26 provided by the present invention are permanently affixed to the belts 18 in a fixation area FA. The unaffixed portions, or free ends, of the adjustment strips 26 may be pulled around the user's waist and releasably attached to another part of the garment 10 to tighten the garment 10 around the user. The free ends may be releasably attached directly to the main body of the garment, the backsheet 12, or to an adjuster attachment area 28. In one embodiment, the adjustment strips 26 may be attached, detached, and reattached many times without losing their ability to provide an adequate gripping force. In another embodiment, the adjustment strips 26 may be adjusted while the garment 10 is being worn.

The adjustment strips 26 depicted in FIG. 2 have gripping connectors 44 attached to them. The gripping connectors 44 are selected to releasably attach to the backsheet 12 or to one or more adjuster attachment areas 28, which are disposed on the backsheet 12 of the garment 10. In one embodiment, the gripping connectors 44 and adjuster attachment area 28 may comprise respective portions of a hook and loop type fastener system. In another embodiment of the invention, the adjustment strips 26 may have integrated gripping portions, abrogating the need for separate gripping connectors 44. For example, the adjustment strips 26 may be tapes of type fastener material that have been permanently affixed to the belts 18 in the fixation area FA. In such an embodiment, the hooks may be removed from the adjustment strips 26 in the fixation area FA to facilitate the creation of a permanent bond between the adjuster strips 26 and the belts 18.

In another embodiment of the invention the adjustment strips 26 comprise adhesive tapes. The adhesive tapes may have a protective covering, such as a silicon sheet, applied to the adhesive surfaces to protect the adhesive surfaces from being contaminated prior to use. The protective coverings may be removed just prior to being adhered to the main body of the garment or to an adjuster attachment area 28 or areas.

The adjustment strips 26 may comprise cloth, film, nonwoven material, or any other suitable material. In one embodiment, the adjustment strips 26 comprise strips of nonwoven material having relatively little elastic extensibility and having a good tactile impression that is comfortable to the touch and will not irritate a user's skin, such as a laminate of spun-bonded material and meltblown polypropylene or meltblown polyethylene. A gripping connector 44 may be attached to each adjustment strip 26 to provide the necessary holding ability. In another embodiment, the adjustment strips 26 may comprise elastic material sandwiched between layers of nonwoven material, or other extensible materials, to provide for elastically extensible adjustment strips 26.

Although the adjustment strips 26 have been described herein in terms of hook and loop type fasteners and adhesive fasteners, it is readily understood to one skilled in the art that any other suitable attachment methods may be used to connect the adjustment strip 26 to the main body of the garment. It should also be understood that such adjustment strips 26 may be selected to attach directly to the backsheet 12 or to a suitable adjuster attachment area 28 that is disposed on the main body of the garment.

Figure 3:
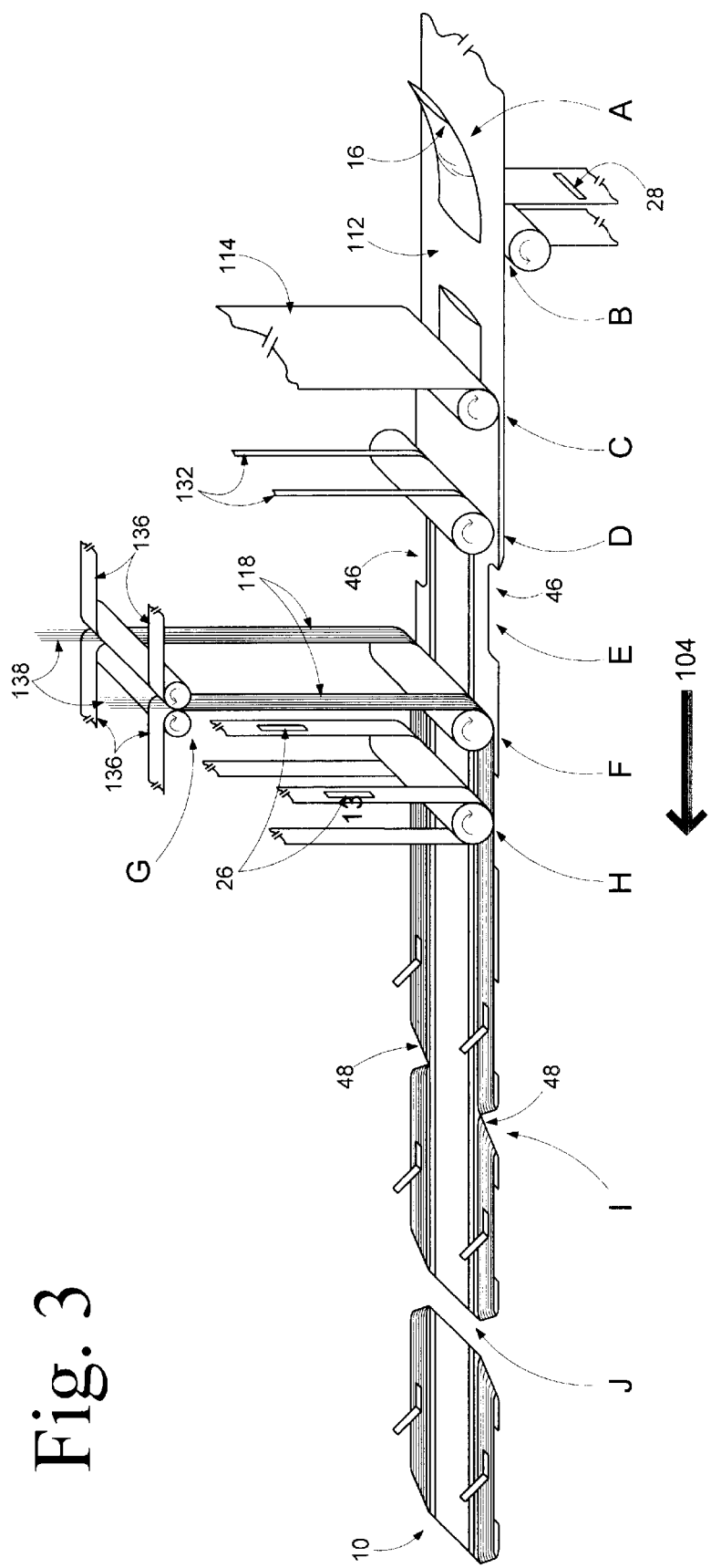
FIG. 3 depicts an embodiment of a manufacturing process for producing a garment of the present invention.

FIG. 3 depicts an embodiment of a manufacturing process for producing a garment having the desired features of the present invention. The various parts of the garment are described in more detail elsewhere herein.

In the preferred embodiment depicted in FIG. 3, a continuous supply of backsheet material 112 is provided along the machine direction 104. At location A, absorbent cores 16 are deposited on the backsheet material 112 on the surface that will eventually become the inner surface of the backsheet 12 of the garment 10. The absorbent cores 16 may be bonded or otherwise operatively associated with the backsheet material 112 at this point or thereafter.

At location B, a supply of adjuster attachment areas 28 is deposited on and operatively associated with the backsheet material 112 on what will become the outer surface of the backsheet 12 of the garment 10. At location C, a continuous supply of topsheet material 114 is provided substantially in the machine direction 104 to overlay the backsheet material 112 and encase the absorbent cores 16. The topsheet material 114 may be adhesively bonded to, or otherwise operatively associated with, the backsheet material 112 or other parts of the assembly at this location or hereafter. At location D, two continuous supplies of standing leg gather material 132 are provided in substantially the machine direction 104, and are attached to the topsheet material 114 inboard of the lateral edges of the topsheet material 114.

At location E, the topsheet material 114 and backsheet material 112 are preferably cut to form leg-hole cutouts 46 on each side of the assembly. Any suitable cutting device may be used, such as fixed blades, cutting drums or reciprocating cutters. The topsheet material 114 and backsheet material 112, and any other components may also be operatively associated with one another during the same operation. For example, a single device may provide blades to cut the leg hole cutouts 46, and also provide anvils to form ultrasonic bonds or heated elements to activate adhesives previously deposited on one or more of the parts.

At location F, two continuous supplies of elastic side belt material 118 are extended to between approximately 100% and approximately 350% of their relaxed length and provided substantially in the machine direction 104 to overlay the assembly. The outer edge of each supply of belt material 118 is substantially adjacent to the corresponding lateral edge of the assembly. In the embodiment depicted in FIG. 3, the supplies of belt material 118 preferably are provided to the main assembly as pre-formed assemblies of supplies of elastic elements 138 and supplies of layers of sheet material 136, which are assembled at location G. In another embodiment, the supplies of elastic elements 138 and supplies of layers of sheet material 136 may be assembled at location F, simultaneously with being deposited on the main assembly.

At location H, a supply of adjustment strips 26 is deposited on and operatively associated with each supply of elastic side belt material 118 on what will eventually become the outer surfaces of the belts 18 of the garment 10.

At location I, each of the continuous supplies of elastic belt material 118 is operatively associated with the main body of the garment in joining areas 48 proximal to each lateral edge of the assembly. Once the garment is severed from the assembly, the joining areas 48 become the seams 24 (FIG. 1) between the main body of the garment and the elastic side belts 18. In one embodiment of the invention, the joining areas comprise V-shaped regions having the open portions of the V shapes adjacent to the lateral edges of the assembly, and the point of the V shape adjacent to the interior edge of each supply of elastic belt material 118. The joining areas 48 may also be made in other shapes, such as a U shape or a modified V shape in which the "legs" of the V are oriented at different angles relative to the machine direction 104.

Excess material created by the joining areas may also be removed from the assembly at location I by any suitable means, as is depicted in FIG. 3. However, excess material may also be removed at another location along the assembly, or not at all. In one embodiment of the invention, the joining areas are created and the excess material is removed in one simultaneous operation by a single device.

Finally, at location J, individual articles 10 are severed from the assembly. This step may also be performed at location I in an operation simultaneous with the creation of the joining areas 48 and the removal of the excess material, or at any other suitable location.

One skilled in the art will understand that the locations of the various parts of the invention during the assembly process, and the intervals at which parts are placed on the assembly, are selected such that the various parts are in their proper location in the final products. In addition, other parts, such as leg gathers 30, may be incorporated into the assembly during the assembly process, and other processes, such as folding and packaging, may be incorporated into the assembly process. Also, it should be understood that any suitable method may be used to introduce the various parts to the assembly line, such as rollers, vacuum drums, or reciprocating stamps. Finally, it should also be understood that the order of the various steps may be modified, combined, or rearranged to provide for various assembly sequences that will provide substantially the same finished product, and all such variations are within the scope and spirit of the present invention and are within the knowledge and skill of those skilled in the art in light of the present teachings. For example, application of topsheet material 114 may take place subsequent to location F, or just prior to location F. Other modification will be apparent to those skilled in the art.

Although the present invention has been described in terms of particular embodiments, it is not limited to these embodiments. Alternative embodiments and modifications which would still be encompassed by the invention may be made by those skilled in the art, particularly in light of the foregoing teachings. Therefore, the following claims are intended to cover any alternative embodiments, modifications or equivalents that may be within the spirit and scope of the invention as defined by the claims.

We claim:

1. An absorbent garment comprising:
a main body having a longitudinal axis corresponding approximately with the front-to-rear axis of a user, a lateral axis orthogonal to the longitudinal axis, the main body comprising a perimeter defined by laterally extending front and rear waist edges, longitudinally extending left and right side edges, left angular edges joining the longitudinally extending left side edge to the front waist edge and the rear waist edge, right angular edges joining the longitudinally extending right side edge to the front waist edge and the rear waist edge, wherein the left and right angular edges each extend at an angle relative to the longitudinal axis; the main body further comprising a substantially liquid impervious backsheet, a substantially liquid pervious topsheet, and an absorbent core disposed between the backsheet and the topsheet;
a left elastic side belt operatively associated with each of the left angular edges; and
a right elastic side belt operatively associated with each of the right angular edges.

2. The absorbent garment of claim 1, wherein the absorbent core comprises airlaid cellulosic material and superabsorbent polymer.

3. The absorbent garment of claim 1, wherein the main body further comprises leg gathers disposed proximal to each of the left and right side edges, each leg gather comprising one or more elastic elements operatively associated with the main body.

4. The absorbent garment of claim 1, wherein the main body further comprises one or more standing leg gathers disposed on a surface of the main body inboard of each of the left and right side edges.

5. The absorbent garment of claim 1, wherein the left and right elastic side belts are elastically extended when the absorbent garment is laid flat.

6. The absorbent garment of claim 1, wherein the angles at which the angular edges extend relative to the longitudinal axis are selected to cause the absorbent garment to have an improved fit on a user when compared to an absorbent garment that does not include angular edges.

7. The absorbent garment of claim 1, wherein the angles at which the angular edges extend relative to the longitudinal axis are between about 10 degrees and about 80 degrees.

8. The absorbent garment of claim 1, wherein the angles at which the angular edges extend relative to the longitudinal axis are between about 30 degrees and about 60 degrees.

9. The absorbent garment of claim 1, wherein the angle at which the angular edges extend relative to the longitudinal axis is about 45 degrees.

10. The absorbent garment of claim 1, further comprising an adjustment strip operatively associated with each of the left and right elastic side belts.

11. The absorbent garment of claim 10, wherein the adjustment strip comprises a portion of a hook and loop fastener.

12. The absorbent garment of claim 1, wherein the main body further comprises one or more adjuster attachment areas.

13. The absorbent garment of claim 12, wherein the one or more adjuster attachment areas comprise a portion of a hook and loop fastener.

14. The absorbent garment of claim 12, further comprising an adjustment strip operatively associated with each of the left and right elastic side belts, wherein the adjustment strips are removably attachable to the one or more adjuster attachment areas.

15. The absorbent garment of claim 14, wherein the adjustment strip comprises one portion of a hook and loop fastener and the one or more adjuster attachment areas comprise the other portion of a hook and loop type fastener.

16. The absorbent garment of claim 14, wherein the adjustment strips allow adjustment in the fit of the absorbent garment on a user.

17. The absorbent garment of claim 14, wherein the adjustment strips may be operated while the user is wearing the absorbent garment.

\* \* \* \* \*